(12) United States Patent
Rösener

(10) Patent No.: US 11,525,107 B2
(45) Date of Patent: Dec. 13, 2022

(54) PROCESS FOR THE PURIFICATION OF ALCOHOL-CONTAINING SOLVENTS

(71) Applicant: SAFECHEM Europe GmbH, Düsseldorf (DE)

(72) Inventor: Christian Rösener, Düsseldorf (DE)

(73) Assignee: SAFECHEM Europe GmbH, Düsseldorf (DE)

(*) Notice: Subject to any disclaimer, the term of this patent is extended or adjusted under 35 U.S.C. 154(b) by 0 days.

(21) Appl. No.: 17/533,427

(22) Filed: Nov. 23, 2021

(65) Prior Publication Data

US 2022/0259525 A1 Aug. 18, 2022

(30) Foreign Application Priority Data

Feb. 16, 2021 (EP) ..................................... 21157268

(51) Int. Cl.
| | | |
|---|---|---|
| B01D 3/00 | (2006.01) | |
| C11D 11/04 | (2006.01) | |
| B01J 13/08 | (2006.01) | |
| C11D 7/26 | (2006.01) | |
| C11D 7/50 | (2006.01) | |
| C11D 11/00 | (2006.01) | |

(52) U.S. Cl.
CPC .............. *C11D 11/04* (2013.01); *B01D 3/009* (2013.01); *B01J 13/08* (2013.01); *C11D 7/261* (2013.01); *C11D 7/263* (2013.01); *C11D 7/5022* (2013.01); *C11D 11/0029* (2013.01)

(58) Field of Classification Search
CPC .......... B01D 3/009; B01J 13/08; C11D 7/261; C11D 7/263; C11D 7/5022; C11D 11/04; C11D 11/0029
See application file for complete search history.

(56) References Cited

U.S. PATENT DOCUMENTS

| | | | | |
|---|---|---|---|---|
| 6,979,669 B2* | 12/2005 | Raehse | ................ | C11D 3/2079 252/186.25 |
| 2009/0176686 A1* | 7/2009 | Tribelhorn | .............. | C07C 41/46 252/364 |
| 2013/0306463 A1* | 11/2013 | Halas | ...................... | C02F 1/048 202/185.1 |
| 2013/0334104 A1* | 12/2013 | Halas | ...................... | B01D 3/02 203/99 |
| 2018/0148673 A1* | 5/2018 | Fernandez-Prieto | .. | C11D 3/382 |

FOREIGN PATENT DOCUMENTS

| | | |
|---|---|---|
| EP | 1 042 257 B1 | 10/2000 |
| EP | 1 907 505 B1 | 4/2008 |
| GB | 675 995 A | 7/1952 |
| WO | 2007/011444 A1 | 1/2007 |

OTHER PUBLICATIONS

Extended European Search Report for EP 21157268.0 dated Jul. 23, 2021 and English Translation, 10 pages.
Kröhnke et al., "Antioxidants" Ullmann's Encyclopedia of Industrial Chemistry; Wiley-VCH Verlag GmbH & Co. KG, Weinheim; pp. 1-36 (2015).

* cited by examiner

*Primary Examiner* — Jonathan Miller
(74) *Attorney, Agent, or Firm* — Rankin, Hill & Clark, LLP; Christopher J. Korff

(57) ABSTRACT

A process for processing an alcohol-containing solvent is described. The process according to the invention is used in particular for the treatment of alcohol-containing solvents which are used, for example, for cleaning metal parts. Further subject matter of the present invention are compositions which are suitable for the aforementioned intended use, as well as the use of certain compositions for the purification of alcohol-containing solvents.

13 Claims, No Drawings

PROCESS FOR THE PURIFICATION OF ALCOHOL-CONTAINING SOLVENTS

CROSS-REFERENCE TO RELATED APPLICATIONS

This application claims priority to European Patent Application No. 21157268.0 filed Feb. 16, 2021, which is hereby incorporated by reference in its entirety.

The present invention relates to a process for purifying an alcohol-containing solvent. The process according to the invention is used in particular for the purification of alcohol-containing solvents which are used, for example, for cleaning, in particular degreasing, metal parts. Further subject-matter of the present invention are compositions which are suitable for the above-mentioned intended use, as well as the use of certain compositions for the purification of alcohol-containing solvents.

When degreasing metal parts using solvents containing alcohol, the solvents containing alcohol may become acidic. Acidification can lead to corrosion damage in the equipment used and may cause damage of metal parts to be degreased in the further course of use.

In order to avoid these disadvantages in the prior art, so-called stabilizers are often added to the alcohol-containing solvents, whereby the stabilizers are used to reduce the acid formation or to bound the formed acid.

Various stabilizers are known from the prior art, for example compositions based on amines and hydrocarbons (cf. EP 1 042 257 A and EP 1 907 505 A, whereby EP 1 042 257 A describes the use of amines for the stabilization only for halogenated hydrocarbons, such as perchloroethylene, and EP 1 907 505 A describes stabilizers for mixtures of modified alcohols and hydrocarbons).

Nevertheless, after certain production cycles, it is necessary to reprocess (clean) or discard the solvent containing alcohol. That said, the user usually discard the solvent bath when a certain limit concentration of impurities (acid, ester, etc.) is reached, which leads to plant downtime and costs for disposal and refilling. New innovative processes that are efficient and easy to carry out are required for the reprocessing of the solvent containing alcohol.

The object of the present invention is, therefore, to provide an efficient and easy-to-perform process for the purification of an alcohol-containing solvent, which is used in particular in the degreasing of metal parts.

This object is solved by a process for purifying an alcohol-containing solvent, which is characterized by introducing into the alcohol-containing solvent a cleaning agent which is present in an encapsulation substantially completely surrounding the cleaning agent.

The cleaning agent encapsulated in this process is used to purify the alcohol-containing solvent and, in particular, to remove the acidification of the alcohol-containing solvent.

In the context of the present invention, it was found that the effect of the cleaning agent for purifying the alcohol-containing solvent can be efficiently improved if the cleaning agent is not introduced directly into the alcohol-containing solvent, but is present in an encapsulation, and that the cleaning agent is introduced in this encapsulated form into the alcohol-containing solvent to be purified, and is released in the alcohol-containing solvent by dissolving the encapsulation.

Without being bound to a theory, it is assumed that the efficiency of the cleaning agent provided according to the invention is improved compared to an unencapsulated material, since there is a slow release of the cleaning agent in the alcohol-containing solvent.

In this regard, it is preferably provided in the present invention that the cleaning agent is present in an encapsulation material that is soluble in the alcoholic solvent such that the substantially encapsulated cleaning agent is released into the alcoholic solvent with dissolution of the encapsulation.

The rate of release of the cleaning agent and thus the rate of dissolution of the encapsulation does not play a significant role for the process according to the invention, but under usual application temperatures of about 100° C. it is in general 1 to 120 minutes, more preferably 1 to 60 minutes, still more preferably 1 to 30 minutes, still more preferably 1 to 10 minutes, still more preferably 3 to 5 minutes.

In the context of the present invention, it is preferably a matter of the correct selection of a suitable encapsulation material. The encapsulation material provided according to the invention should preferably dissolve in the alcohol-containing solvent in the first place, if necessary at elevated temperature. A further requirement to be met preferably by the encapsulation material in the context of the present invention is that the encapsulation material dissolves in the alcohol-containing solvent and no disturbing impurities are formed in the process. Furthermore, it is advantageous for the present invention if the encapsulation material can be easily produced and enables simple and efficient encapsulation, as completely as possible, of the cleaning agent according to the invention.

Stabilizers, such as those known from the prior art, are usually provided in liquid form and consist of mixtures of liquids or solids dissolved in liquids.

Powdered substances, on the other hand, have not yet been used on a large scale so far. These can cause a dust explosion if the substance is swirled in the air and ignition sources are present. In the case of dusts, it is difficult to avoid explosive mixtures by limiting the dust concentration.

The encapsulation of the powdered cleaning agent therefore provides a new way of purifying solvents containing alcohol, since the encapsulation prevents dangerous turbulence of the substance in the air.

In this context, the encapsulation material should be preferably as non-toxic as possible, so that users of the process according to the invention can add the encapsulation material to the solvent without explosion protection measures and minor safety measures, i.e. without wearing personal protective equipment to prevent dermal and inhalation exposure. Furthermore, it is advantageous for the selection of a suitable encapsulation material if the material is transparent, so that it is easy to inspect the cleaning agent before its application in the alcoholic solvent to be cleaned.

Finally, the encapsulation material should be able to contain different amounts of cleaning agent so that an appropriate dosage can be easily selected and used by the operator of the process according to the invention.

Within the scope of the present invention, numerous different encapsulation materials have been investigated for this application, and suitable materials for the formation of the encapsulation include preferably cellulose derivatives, in particular cellulose esters, such as cellulose nitrate, cellulose acetate or cellulose acetate butyrate, and polyvinyl butyral.

With regard to the cellulose derivatives, the skilled person can find suitable cellulose derivatives that are soluble in alcohol-containing solvents under the conditions to be used according to the invention on the basis of the solubility behavior, the nature of the substituents, the average degree of substitution, the substitution distribution in the chain and their distribution among the primary and secondary alcohol groups for different alcohol-containing solvents.

Another suitable material for forming the encapsulation is polyvinyl butyral (PVB). Polyvinyl butyrals with highly acetalized settings (high degree of acetalization) are especially alcohol soluble. For the formation of the packaging material, it is particularly preferred if the polyvinyl butyral can be processed into films with a low dynamic viscosity.

Corresponding commercially available starting materials for the production of the encapsulation are sold commercially by the company Kuraray Europe GmbH, for example. Suitable commercial products are, for example, Mowital® B30H or Mowital® B20H.

In the context of the present invention, polyvinyl butyral is particularly preferred as an encapsulation material. The reasons for this are explained below:

First of all, polyvinyl butyral is thermoplastic processable, light-stable and heat-sealable at temperatures above 120° C. Therefore, in the context of the present invention, it is easy to produce film materials for making encapsulated cleaning agents from these encapsulation materials, for example in the form of pouches.

The desired encapsulation based on polyvinyl butyral also has the advantage that the resulting encapsulation is clear and transparent, so that it is possible to inspect the encapsulated cleaning agent before it is used to treat the alcohol-containing solvent.

Another significant advantage of using polyvinyl butyral as encapsulation material is that the polyvinyl butyral dissolves easily under the process conditions used and no interfering by-products are introduced into the alcohol-containing solvent to be purified.

In a preferred embodiment of the present invention, the encapsulation material comprises not only polyvinyl butyral and other polymers, but consists essentially, in particular exclusively, of polyvinyl butyral. In the context of the present invention, therefore, in a preferred embodiment, an encapsulation material consisting essentially, in particular exclusively, of polyvinyl butyral is provided.

In the following, particularly preferred embodiments of the polyvinyl butyral preferred according to the present invention as encapsulation material are described.

The polyvinyl butyral preferably used in the present invention generally has a polyvinyl alcohol content of from 11 to 27% by weight, based on the total mass of polyvinyl butyral.

In this context, it is further and independently preferred if the polyvinyl butyral has a polyvinyl acetate content. It is further preferred if the content of polyvinyl acetate in the polyvinyl butyral is up to 8% by weight, based on the total mass of polyvinyl butyral.

Regardless of the above properties of the polyvinyl butyral preferred to be used, this encapsulation material preferably has a dynamic viscosity of 9 to 330 mPa·s in a 10% solution in ethanol.

Regardless of the above properties of the polyvinyl butyral to be preferably used, this encapsulation material preferably has a water absorption capacity of the polyvinyl butyral after 24 hours at 20° C. of 200 to 340 g/l.

Regardless of the above properties of the polyvinyl butyral preferred to be used, this encapsulation material preferably has a glass transition temperature, determined according to DSC, IS011357-1, of from 60 to 92° C.

Irrespective of the above properties of the polyvinyl butyral to be used in preference, this encapsulation material preferably has a solids content of more than 97.5% by weight.

The above-described properties of the polyvinyl butyral make it particularly suitable for use as a capsule material in the process according to the invention.

Particularly preferred embodiments of the present invention according to the present invention use polyvinyl butyral, which has more than one of the properties described above. In particular, the polyvinyl butyral to be used according to the invention exhibits at least 2, more preferably at least 3, more preferably at least 4, more preferably at least 5, of the properties described above.

The cleaning agent present in the encapsulation within the scope of the present invention preferably comprises a base. With the help of the base as a cleaning agent, acidic impurities that arise during the use of the alcohol-containing solvent are neutralized and thus rendered harmless for the further use of the alcohol-containing solvent.

In a preferred embodiment, the cleaning agent consists essentially, in particular exclusively, of a base.

The use of multiple bases as cleaning agents is also encompassed by the present invention. In case more than one base is used, these bases can be used in parallel and can be encapsulated together in one encapsulation or can be encapsulated separately.

In addition, the cleaning agent may comprise other ingredients that are also used to clean the alcohol-containing solvent.

Should a base be used as a cleaning agent in the context of the present invention, the alcohol-containing solvent preferably has an acid as an impurity. In addition, non-specific esterification products can also form from the acid present as an impurity, which are removed from the alcohol-containing solvent by the encapsulated detergent.

In another embodiment of the present invention, the cleaning agent used in the encapsulation is hygroscopic. By using a hygroscopic cleaning agent, aqueous impurities can also be efficiently separated by the process according to the invention, in addition to acidic impurities. Aqueous impurities can form, for example, due to non-specific ester formations from the acid impurity with the alcohol in the alcohol-containing solvent.

However, the use of a hygroscopic cleaning agent and the presence of water as an impurity in the alcoholic solvent are not mandatory for the present invention.

In a preferred embodiment of the present invention, the cleaning agent is preferably a base selected from the group consisting of alkali metal or alkaline earth metal hydroxides and mixtures thereof.

In a preferred embodiment of the present invention, the cleaning agent is selected from the group consisting of sodium carbonate, potassium carbonate, sodium hydroxide, potassium hydroxide, sodium hydrogen carbonate, calcium hydroxide, magnesium carbonate, and mixtures of the foregoing cleaning agents.

In another preferred embodiment of the present invention, the cleaning agent is selected from the group consisting of sodium carbonate, potassium carbonate, sodium hydroxide, potassium hydroxide, and mixtures of the foregoing cleaning agents.

After bringing the alcohol-containing solvent to be purified into contact with the encapsulated cleaning agent, the alcohol-containing solvent to be purified is distilled (refluxed) within the scope of the present invention.

This distillation or this refluxing of the alcohol-containing solvent is preferably carried out for a period of at least 1 hour, preferably at least 2 hours, more preferably at least 3 hours, more preferably at least 6 hours, more preferably at least 12 hours, more preferably at least 24 hours. Due to the temperatures used in combination with the detergent used, efficient removal of contaminants from the alcohol-based solvent occurs.

In practice, the process according to the invention can be carried out by adding the encapsulated cleaning agent to the bottom of a distillation unit (refluxing device) provided with the solvent to be purified and then using it at the temperatures provided for in the present invention.

Alternatively, it is also possible to supply the encapsulated cleaning agent at any other point of the unit or device used. Any other places are, for example, a water separator used.

However, in the context of the present invention, it has been found to be technically most useful for the encapsulated detergent to be added to the sump, since a solid must be separated.

In the context of the present invention, at least one or more antioxidants may be used in addition to the encapsulated detergent. This antioxidant is added to the alcohol-containing solvent before or during contact with the encapsulated cleaning agent.

Suitable antioxidants that can be additionally used during the process of the invention to purify the alcohol-containing solvent are, for example, phenolic antioxidants, amine-containing antioxidants, antioxidants based on organic sulfur compounds, antioxidants based on organic phosphorus compounds and mixtures of the aforementioned antioxidants.

Corresponding antioxidants are known to those skilled in the art from *Ullmann's Encyclopedia of industrial chemistry*, Chapter: Antioxidants (2015, Wiley-VCH Verlag GmbH & Co. KG, Weinheim). In particular, suitable antioxidants can be found in chapters 4.2, 4.3, 4.4 and 4.5.

In a first embodiment, the antioxidant is a phenolic antioxidant.

In a second embodiment, the antioxidant is an amine-containing antioxidant.

In a third embodiment, the antioxidant is an antioxidant based on organic sulfur compounds.

In a fourth embodiment, the antioxidant is an organic phosphorus compound-based antioxidant.

Particularly suitable antioxidants are selected from the group consisting of 2,6-di-tert-butyl-4-methylphenol, 2,6-di-tert-butylphenol and mixtures thereof.

Other suitable antioxidants are selected from the group consisting of p,p'-dioctyldiphenylamine, oligomeric 1,2-dihydro-2,2,4-trimethylquinoline, 1-naphthylphenylamine, derivatives of diphenylamine, and mixtures thereof.

These antioxidants are preferably used together with the detergent in the encapsulation substantially completely surrounding the detergent or may be added separately to the alcohol-containing solvent.

In a further embodiment of the present invention, the cleaning agent is used encapsulated optionally in combination with at least one antioxidant as well as additionally with silica gel as a surface-active substance.

The process according to the invention is used in particular for alcohol-containing solvents resulting from (metal) degreasing plants. (Metal) degreasing systems are usually closed systems, which include a cleaning chamber, a varying number of solvent tanks, and a distillation unit. By means of a solvent, preferably with modified alcohols defined further below, contaminated parts are cleaned in the cleaning process.

The contaminated solvent containing alcohol, i.e. the solvent enriched with the detached residues of the cleaned and degreased components, then flows back into the solvent tanks. These tanks permanently feed the distillation unit integrated in the degreasing system with the contaminated solvent. During the distillation process, the solvent, which boils earlier respectively at a lower temperature, is separated from the previously purified residues. During this distillation process, acidification may occur due to self-decomposition of the solvent. For example, the use of modified alcohol as a solvent can give rise to low-boiling components and, above all, acids. Acidification can in turn lead to corrosion damage in the cleaning equipment and surface corrosion on the cleaned parts.

To counteract acid formation in the distillation unit, the encapsulated detergent provided according to the invention is added to the distillation process during purification. The cleaning agent binds the acids formed in the distillation sump and remains in the distillation sump. The cleaning agent thus remains in the distillation unit during the entire solvent cleaning and preparation process.

The distillate, i.e. the distilled and purified solvent containing alcohol, is subsequently fed back to the solvent tanks via a water separator, among other things. The distillation sump is emptied and disposed of at regular intervals. The thus used cleaning agent together with possible non-interfering residues from the material of the encapsulation is discharged together with the cleaned residues of the components.

By means of a rapid test procedure for checking solvents, the user can determine the quality, i.e. the acid content, of the solvent used directly at the plant itself.

Knowing the determined acidity of the alcohol-containing solvent, i.e. the proportion of free acids in the alcohol-containing solvent, and the system volume of the degreasing system, the required addition quantity of the cleaning agent according to the present invention can be determined by means of stoichiometric calculation in order to neutralize the acid content.

In the context of the present invention, the alcohol-containing solvent are generally individual modified alcohols or mixtures of modified alcohols.

Modified alcohols are, for example, propanols to which an ether group has been added (alkoxy-propanols). By varying the ether group, the dissolving power of the modified alcohols can be adapted to the type of impurity (degreasing).

The modified alcohols are, for example, glycol ether mixtures and/or glycol ether-hydrocarbon mixtures.

Particularly preferred in the context of the present invention are 1-butoxy-2-propanol and butoxy-1-propanol. Mixtures of these two previously mentioned modified alcohols are also particularly preferred in the context of the present invention.

In another aspect, the present invention relates to a composition comprising a cleaning agent and an encapsulant, preferably used in the process according to the invention described above.

Therefore, the present invention also relates to a composition comprising a cleaning agent in an encapsulation of a polymeric material comprising polyvinyl butyral.

According to the above explanations of the process according to the invention, the cleaning agent in the encapsulation preferably comprises a base or consists essentially, in particular exclusively, of a base.

The encapsulation essentially completely surrounds the cleaning agent.

As stated above, it is preferred if the cleaning agent in the encapsulation is hygroscopic.

In a preferred embodiment of the present invention, the composition is characterized in that the cleaning agent is selected from the group consisting of sodium carbonate, potassium carbonate, sodium hydroxide, potassium hydroxide, sodium hydrogen carbonate, calcium hydroxide, magnesium carbonate, and mixtures of the foregoing cleaning agents.

In another preferred embodiment of the present invention, the cleaning agent is selected from the group consisting of sodium carbonate, potassium carbonate, sodium hydroxide, potassium hydroxide, and mixtures of the foregoing cleaning agents.

As stated above, the capsule material preferably comprises polyvinyl butyral.

In the further preferred embodiment of the present invention, the capsule material consists essentially, in particular exclusively, of polyvinyl butyral.

For the indicated use for degreasing metal parts according to the above process, it is further preferred if the polyvinyl butyral has a polyvinyl alcohol content of 11 to 27% by weight, based on the total mas of polyvinyl butyral.

In a further embodiment, the composition according to the invention is characterized in that the polyvinyl butyral has a content of polyvinyl acetate.

If the polyvinyl butyral in the composition according to the invention has a content of polyvinyl acetate, the content of polyvinyl acetate in the polyvinyl butyral is preferably up to 8% by weight, based on the total mass of polyvinyl butyral.

The dynamic viscosity of the polyvinyl butyral to be used according to the invention is preferably 9 to 330 mPa·s in a 10% solution in ethanol.

The water absorption capacity of the polyvinyl butyral to be used according to the invention after 24 hours at 20° C. is preferably 200 to 340 g/l.

The glass transition temperature of the polyvinyl butyral to be used according to the invention, determined by DSC, ISO11357-1, is preferably 60 to 92° C.

The solids content of the polyvinyl butyral to be used according to the invention is preferably more than 97.5% by weight.

In the composition according to the invention, in addition to the actual cleaning agent, the base described in more detail above, at least one or more antioxidants may also be used.

Corresponding antioxidants are known to those skilled in the art from *Ullmann's Encyclopedia of industrial chemistry*, Chapter: Antioxidants (2015, Wiley-VCH Verlag GmbH & Co. KG, Weinheim). In particular, suitable antioxidants can be found in chapters 4.2, 4.3, 4.4 and 4.5.

In a first embodiment, the antioxidant is a phenolic antioxidant.

In a second embodiment, the antioxidant is an amine-containing antioxidant.

In a third embodiment, the antioxidant is an antioxidant based on organic sulfur compounds.

In a fourth embodiment, the antioxidant is an organic phosphorus compound-based antioxidant.

Particularly suitable antioxidants are selected from the group consisting of 2,6-di-tert-butyl-4-methylphenol, 2,6-di-tert-butylphenol and mixtures thereof.

Other suitable antioxidants are selected from the group consisting of p,p'-dioctyldiphenylamine, oligomeric 1,2-dihydro-2,2,4-trimethylquinoline, 1-naphthylphenylamine, derivatives of diphenylamine, and mixtures thereof.

Furthermore, the present invention relates to the use of the composition described above for the purification of a solvent that is used in particular for degreasing metal parts. Reference is made to the above explanations.

Furthermore, the present invention relates to a process for the preparation of a composition according to the invention, the details of which have been described above. The method according to the invention is characterized by the following process steps:

i. providing a film comprising polyvinyl butyral;
ii. providing a cleaning agent;
iii. sealing the substance into the film comprising polyvinyl butyral such that the substance is in a substantially completely surrounding encapsulation.

In this process, encapsulation is performed by welding the film at a temperature of at least 120° C.

For further details, reference is made to the above.

The following examples illustrate the present invention in detail, but are not be intended to limit the scope of the invention.

EXAMPLES

Test 1: Simple Mixing Test and Evaporation Behavior

A film of Mowital Thin Film 100 is mixed with solvent (DOWCLENE® 1601) at room temperature; the solvent is then evaporated.

Analytical Results:

1. Solubility: Without agitation, complete dissolution of the plastic was observed after approximately 30 minutes.

2. Appearance after evaporation: The solvent was evaporated at 80° C. overnight. A uniform, colorless Mowital film formed in the container.

Evaluation:

The solubility of the film is good and the recovery shows that the plastic shows no obvious degradation reactions due to the applied temperature and solvent and the combination thereof.

Test 2: Endurance Test in Laboratory Distillation Apparatus with Fresh DOWCLENE® 1601

Mowital Thin Film 100 in a solvent (DOWCLENE® 1601) are mixed in the distillation sump of the laboratory apparatus. Metal strips made of aluminum, steel, copper and brass are suspended in the steam space of the apparatus. The solvent is continuously refluxed in negative pressure (100 mbar) for 6 days.

Evaluation:

1. GC/FID analysis of the distillate: solvent was recovered in unchanged purity. Volatile organic degradation products from the plastic were not identified.

2. Acidity of the distillate (titration method): The solvent was unchanged and within specification.

3. Optical inspection of the metal strips: The metal strips showed no coating, or similar plastic-like precipitation.

4. Assessment of the sump: The sump appeared viscous, which was triggered by the high concentration of PVB. Clumping or caking of the plastic was not observed. The color was unchanged.

5. FT-IR analysis of the sump: After the experiment, the solvent in the distillation residue was evaporated. An FT-IR spectrum of the plastic remaining in the sump was recorded and compared to an unused plastic film. There was no change between the dissolved, heated plastic after the test and the originally unused film.

Evaluation:

No potentially troublesome degradation products show up even at permanently high temperatures in the boiling solvent. The plastic was dissolved by the solvent, but was chemically unchanged. The solvent distilled from the sump corresponds to the fresh material used and can be used without restriction for cleaning.

Test 3: Endurance Test in Laboratory Distillation Apparatus with Acidic DOWCLENE® 1601

The above experiment 2 was repeated with Mowital granules B30H and with acid solvent (acid number about 6000 ppm).

Analytical Results:

1. GC/FID analysis of the distillate: Only solvent of unchanged quality was recovered. Volatile organic degradation products from the plastic were not identified.

2. Acidity of the distillate (titration method): The acid number remained constant.

3. Optical inspection of the metal strips: The metal strips showed no coating, or similar plastic-like precipitation.

4. Assessment of the sump: The sump showed discoloration. This is often observed during distillation of acidic samples. Clumping or caking of the plastic was not observed.

Evaluation:

The findings obtained for a fresh solvent are identical for an acidic solvent: No degradation products of the plastic were observed; the solvent distillate corresponds in quality to the solvent used and can be used for cleaning.

Experiment 4: Acid Reduction Using Encapsulated Detergent—Sample 1

Acidic DOWCLENE® 1601 (solvent taken from customer cleaning plant as the most realistic example possible) are refluxed overnight at 100 mbar. Metal strips of aluminum, steel, copper and brass are suspended in the steam space of the apparatus. The next day, a sample is taken at the sampling point in the distillate for zero determination.

The encapsulated cleaning material is produced by sealing anhydrous sodium carbonate and adding an antioxidant in a Mowital Thin Film 100 film.

The encapsulated detergent is added to the sump to reduce the acid. The film dissolves in hot solvent within 3 to 5 minutes and releases the solid, which disperses finely.

The solvent is refluxed for an additional 6 hours, at which time the detergent complexes the acid in the sump. To evaluate the success, further samples are taken after 2, 4 and 6 hours. The distillation capacity of the apparatus is approx. ⅓ of the total solvent volume per hour.

Analytical Results:

1. Acidity of the distillate (titration method):
Zero value: 9853 ppm as acetic acid
After 2 h (⅔ times circulation of the volume): 2761 ppm
After 4 h (4/3 times circulation of the volume): 1510 ppm
After 6 h (2-fold circulation of the volume): 578 ppm 2. GC/FID analysis: The distillate showed consistent quality at all sampling times, with the exception that the acetic acid signal showed a drop in intensity after 6 hours that was associated with the titration result.

3. Ion chromatographic analysis of the distillate after 2 hours: A concentration of acetate and formate matching the acid concentration (2761 ppm) was measured (2190 mg/L acetate, 440 mg/L formate). No other anions were identified.

4. Optical inspection of the metal strips: The metal strips showed no coating or similar plastic-like deposits.

5. Assessment of the sump: The sump showed finely dispersed white solid. No clumping or caking of the solid or plastic was observed. The solid is soluble in water.

Evaluation:

The encapsulated detergent showed a significant reduction in acid number after even a short test period. The solid did not clump and disposal of the solid was easy due to its water solubility.

The solvent distillate is unchanged from the starting material, with the exception that the acid has been removed. The solvent can thus continue to be used for cleaning and gains significantly in value due to the acid removal, since corrosive components are removed.

Experiment 5: Acid Reduction Using Encapsulated Detergent—Sample 2

Acidic DOWCLENE® 1601 (solvent taken from customer's cleaning plant as the most realistic example possible) is refluorinated for 2 hours at 100 mbar. Metal strips made of aluminum, steel, copper and brass are suspended in the steam space of the apparatus. After 2 hours, a sample is taken at the sampling point in the distillate for zero determination.

The encapsulated detergent is produced by sealing anhydrous sodium carbonate and adding an antioxidant in Mowital Thin Film 100 film.

The encapsulated detergent is added to the sump to reduce the acid. The film dissolves in hot solvent within 3 to 5 minutes and releases the solid, which disperses finely.

The solvent is refluxed for a further 24 hours, with the detergent complexing the acid in the sump. Further samples are taken after 2 and 24 hours to assess success. The distillation capacity of the apparatus is approximately ⅓ of the total solvent volume per hour.

Analytical Results

1. Acidity of the distillate (titration method):
Zero value: 6303 ppm as acetic acid
After 2 h (⅔ times circulation of the volume): 3009 ppm
After 24 hrs (8 times circulation of the volume): <10 ppm 2. GC/FID analysis: The distillate showed consistent quality at all sampling times, with the exception that the acetic acid signal showed a drop in intensity after 24 hours that was associated with the titration result.

3. Ion chromatographic analysis of the distillate after 2 hours: An amount of acetate and formate approximately matching the acid concentration (3009 ppm) was identified (1550 mg/L acetate, 940 mg/L formate). No other anions were identified.

4. Optical inspection of the metal strips: The metal strips showed no coating, or similar plastic-like precipitation.

5. Assessment of the sump: The sump showed finely dispersed white solid. No clumping or caking of the solid or plastic was observed. The solid is soluble in water.

Evaluation:

The encapsulated detergent also showed a clear reduction of the acid number up to complete removal after 24 hours. The solid did not clump in the test and disposal of the solid was easy due to its water solubility.

The solvent distillate is unchanged from the starting material, with the exception that the acid has been removed. The solvent can thus continue to be used for cleaning and gains significantly in value due to the acid removal, since corrosive components are removed.

Experiment 6: Acid Reduction Using Encapsulated Detergent—Sample 3

Acidic DOWCLENE® 1601 are refluxed overnight at 100 mbar. Metal strips made of aluminum, steel, copper and brass are suspended in the steam space of the apparatus. The next day, a sample is taken at the sampling point in the distillate for zero determination.

The encapsulated detergent is produced by sealing anhydrous sodium carbonate and adding an antioxidant in Mowital Thin Film 100 film.

To reduce the acid, the encapsulated detergent is added to the sump. The film dissolves in hot solvent within 3 to 5 minutes and releases the solid, which disperses finely.

The solvent is refluxed for a further 6 hours, with the detergent complexing the acid in the sump. Further samples are taken after 2, 4 and 6 hours to assess success. The distillation capacity of the apparatus is approximately ⅓ of the total solvent volume per hour.

Analytical Results:
1. Acidity of the distillate (titration method):
Zero value: 13391 ppm as acetic acid
After 2 h (⅔ times circulation of the volume): 3724 ppm
After 4 h (4/3 times circulation of the volume): 1529 ppm
After 6 h (2-fold circulation of the volume): 537 ppm
2. GC/FID analysis: The distillate showed consistent quality at all sampling times with the exception that the acetic acid signal after 6 hours showed a drop in intensity associated with the titration result.
3. Ion chromatographic analysis of the distillate after 2 hours: A concentration of acetate and formate matching the acid concentration (3724 ppm) in magnitude was measured (3300 mg/L acetate, 1700 mg/L formate). No other anions were identified.
4. Optical inspection of the metal strips: The metal strips showed no coating, or similar plastic-like precipitation.
5. Assessment of the sump: The sump showed finely dispersed white solid. No clumping or caking of the solid or plastic was observed. The solid is soluble in water.

Evaluation:

The encapsulated detergent showed a significant reduction in acid number after even a short test period. The solid did not clump and disposal of the solid was easy due to its water solubility.

The solvent distillate is unchanged from the starting material with the exception that the acid has been removed. The solvent can thus continue to be used for cleaning and gains significantly in value due to the acid removal, since corrosive components are removed.

Comparative Experiment 7: Acid Reduction with the Aid of Unencapsulated Stabilizer The same amount (as in the above experiments) of acidic DOWCLENE® 1601 is refluxed overnight at 100 mbar, with the solvent being the same as in the previous experiments. Metal strips made of aluminum, steel, copper and brass are suspended in the steam space of the apparatus as above. The next day, a sample is taken at the sampling point in the distillate for zero determination.

The detergent is prepared by mixing anhydrous sodium carbonate and an antioxidant. The amounts of anhydrous sodium carbonate and antioxidant are identical to those used in the experiments described above. The detergent is added to the sump in powder form.

The solvent is refluxed for a further 6 hours, with the detergent complexing the acid in the sump. Further samples are taken after 2, 4 and 6 hours to assess success. The distillation capacity of the apparatus is approximately ⅓ of the total solvent volume per hour.

Analytical Results
1. Acidity of the distillate (titration method):
Zero value: 12327 ppm as acetic acid
After 2 h (⅔ times circulation of the volume): 10239 ppm
After 4 h (4/3 times circulation of the volume): 9916 ppm
After 6 h (2-fold circulation of the volume): 9813 ppm
2. GC/FID analysis: The distillate showed consistent quality at all sampling times, with the exception that the acetic acid signal showed a small drop in intensity after 6 hours, which was associated with the titration result.
3. Ion chromatographic analysis of the distillate after 2 hours: A concentration of acetate and formate approximately matching the acid concentration (10239 ppm) was measured (6900 mg/L acetate, 3400 mg/L formate). Further anions were not identified.
4. Optical inspection of the metal strips: The metal strips showed no coating, or similar plastic-like precipitation.
5. Assessment of the sump: The sump showed finely dispersed white solid. No clumping or caking of the solid or plastic was observed. The solid is soluble in water.

Overall Evaluation:

The encapsulated detergent showed a significantly higher reduction of the acid number than the non-encapsulated version. It can therefore be assumed that the encapsulation represents a technical advantage in terms of controlled release of the cleaning agent. Moreover, the encapsulated cleaning agent according to the present invention is easier to be used and does not require any additional safety measurements (due to the encapsulation.

The present invention is once again summarized by the following items:
1. A process for purifying an alcohol-containing solvent, which comprises introducing into the alcohol-containing solvent a cleaning agent which is present in an encapsulation which substantially completely surrounds the cleaning agent.
2. The process according to item 1, characterized in that the capsule material comprises cellulose derivatives and/or polyvinyl butyral.
3. The process according to item 1 or 2, characterized in that the cleaning agent in the encapsulation comprises a base or consists of a base.
4. The process according to any one of items 1 to 3, characterized in that the cleaning agent is selected from the group consisting of sodium carbonate, potassium carbonate, sodium hydroxide, potassium hydroxide, sodium hydrogen carbonate, calcium hydroxide, magnesium carbonate and mixtures of the above cleaning agents.
5. The process according to any one of items 1 to 4, characterized in that the alcoholic solvent is refluxed after being brought into contact with the substantially encapsulated cleaning agent.
6. The process according to any one of items 1 to 5, characterized in that at least one antioxidant is added to the solvent during the process of purifying the alcohol-containing solvent.
7. The process according to any one of items 1 to 6, characterized in that the alcohol-containing solvent contains modified alcohols, in particular glycol ether mixtures.
8. A composition comprising a cleaning agent in a substantially encapsulation of a polymeric material comprising polyvinyl butyral.
9. The composition according to item 8, characterized in that the cleaning agent in the encapsulation comprises or consists of a base.
10. The composition according to item 8 or 9, characterized in that the cleaning agent in the encapsulation is hygroscopic.
11. The composition according to any one of items 8 to 10, characterized in that the cleaning agent is selected from the group consisting of sodium carbonate, potassium carbonate, sodium hydroxide, potassium hydroxide, sodium hydrogen carbonate, calcium hydroxide, magnesium carbonate and mixtures of the above cleaning agents.

12. Use of a composition according to any one of items 8 to 11 for processing alcohol-containing solvents, in particular for cleaning alcohol-containing solvents.

13. The use according to item 12 for cleaning modified alcohols, in particular glycol ether mixtures.

14. A process for preparing a composition according to any one of items 8 to 11, characterized by the following process steps:
   i. providing a film comprising polyvinyl butyral;
   ii. providing a cleaning agent;
   iii. sealing the cleaning agent into the film comprising polyvinyl butyral such that the cleaning agent is in a substantially completely surrounding encapsulation.

15. The process according to item 14, characterized in that the encapsulation is carried out by welding the film at a temperature of at least 120° C.

The invention claimed is:

1. A process for purifying an alcohol-containing solvent comprising:
   introducing a cleaning agent into the alcohol-containing solvent, and
   refluxing the alcohol-containing solvent,
wherein the cleaning agent is in an encapsulation material, and
wherein the encapsulation material completely surrounds the cleaning agent.

2. The process according to claim 1, wherein the encapsulation material comprises at least one of cellulose derivatives and polyvinyl butyral.

3. The process according to claim 2, wherein the encapsulation material comprises polyvinyl butyral and the cleaning agent comprises a base.

4. The process according to claim 3, wherein the base is selected from the group consisting of sodium carbonate, potassium carbonate, sodium hydroxide, potassium hydroxide, sodium hydrogen carbonate, calcium hydroxide, magnesium carbonate and mixtures of the foregoing.

5. The process according to claim 4, wherein the alcohol-containing solvent comprises modified alcohols.

6. The process according to claim 5, wherein the alcohol-containing solvent comprises glycol ether mixtures.

7. The process according to claim 3, wherein the alcohol-containing solvent comprises modified alcohols.

8. The process according to claim 7, wherein the alcohol-containing solvent comprises glycol ether mixtures.

9. The process according to claim 1, wherein the cleaning agent comprises a base.

10. The process according to claim 1, wherein the cleaning agent is selected from the group consisting of sodium carbonate, potassium carbonate, sodium hydroxide, potassium hydroxide, sodium hydrogen carbonate, calcium hydroxide, magnesium carbonate and mixtures of the foregoing.

11. The process according to claim 1, further comprising adding at least one antioxidant to the alcohol-containing solvent.

12. The process according to claim 1, wherein the alcohol-containing solvent comprises modified alcohols.

13. The process according to claim 12, wherein the alcohol-containing solvent comprises glycol ether mixtures.

* * * * *